United States Patent [19]
Dultz et al.

[11] Patent Number: 6,031,588
[45] Date of Patent: *Feb. 29, 2000

[54] FERROELECTRIC LIQUID CRYSTAL DEVICE FOR LOCAL REDUCTION OF LIGHT INTENSITY IN THE VISUAL FIELD

[75] Inventors: Wolfgang Dultz, Frankfurt/M., Germany; Arkadii Onokhov, St. Petersburg; Leonid Beresnev, Moscow, both of Russian Federation; Wolfgang Haase, Reinheim, Germany

[73] Assignee: Deutsche Telekom AG, Bonn, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/838,965

[22] Filed: Apr. 23, 1997

[30] Foreign Application Priority Data

Apr. 24, 1996 [DE] Germany ............ 196 16 323

[51] Int. Cl.$^7$ .................................. G02F 1/135
[52] U.S. Cl. .................. 349/25; 349/13; 348/341; 348/207; 351/44; 345/7
[58] Field of Search .................. 349/13, 25; 348/341, 348/207; 351/44

[56] References Cited

U.S. PATENT DOCUMENTS

| | | | |
|---|---|---|---|
| 4,462,661 | 7/1984 | Witt | 350/331 |
| 4,842,400 | 6/1989 | Klein | 351/158 |
| 4,848,890 | 7/1989 | Horn | 351/44 |

(List continued on next page.)

FOREIGN PATENT DOCUMENTS

| | | |
|---|---|---|
| 0 630 627 | 12/1994 | European Pat. Off. . |
| 0 678 288 | 10/1995 | European Pat. Off. . |
| 2 611 389 | 9/1988 | France . |

(List continued on next page.)

OTHER PUBLICATIONS

Tomilin, M. et al., "Safety Goggles With Local–Space Modulation," *Mol. Cryst. Liq. Cryst.*, 1992, vol. 222, pp. 119–124.

Beresnev, L. et al., "Deformed helix ferroelectric liquid crysta display: a new electrooptic mode in ferroelectric chiral smectic C liquid crystals," *Liquid Crystals*, 1989, vol. 5, No. 4, pp. 1171–1177.

Beresnev, L. et al., "X–Ray And Optical Investigations Of The Dislocation Domains In Ferroelectric Liquid Crystals," pp. 1–13, Figs. 1–14.

Patent Abstracts of Japan 6–148598 (A), P–1791, Aug. 24, 1994, vol. 18, No. 454.

(List continued on next page.)

*Primary Examiner*—William L. Sikes
*Assistant Examiner*—Robert J. Hollingshead
*Attorney, Agent, or Firm*—Kenyon & Kenyon

[57] ABSTRACT

A device featuring liquid crystals for local reduction of the intensity of incident light is described. This device protects the eyes or the video camera against blinding, or the light-sensitive medium against local damage by automatically reducing the intensity of the incident light emitted by brightly illuminated objects, while the brightness of poorly illuminated objects is not suppressed. The device uses optically addressed spatial light modulators (OASLM) on the basis of a semitransparent photoconducting film in contact with ferroelectric liquid crystals (FLC). The DHF effect (deformation of the helix structure) in ferroelectric liquid crystals (FLC) with helix-shaped structure is used here. The drive voltage has a frequency of $10^2$ to $10^3$ Hz at an amplitude of ±20 V, which is 10–50 times higher than that of devices operating with nematic liquid crystals. The device allows moving objects to be observed against the background of a bright light source (sun, lamp, etc.). A switchable shutter on the basis of ferroelectric liquid crystals (FLC) is used at a molecular inclination of $\theta_o \neq 45°$. To increase the average transmission of the device, a second FLC layer with chiral smectic A or C phase with a switchable molecular inclination of $\theta_c = 45° - \theta_o$ or $\theta_c = \theta_o$ is used.

10 Claims, 9 Drawing Sheets

U.S. PATENT DOCUMENTS

| | | | |
|---|---|---|---|
| 4,968,127 | 11/1990 | Russell et al. | 351/44 |
| 5,015,086 | 5/1991 | Okaue et al. | 351/44 |
| 5,056,897 | 10/1991 | Akiyama et al. | 359/72 |
| 5,073,010 | 12/1991 | Johnson et al. | 359/72 |
| 5,081,542 | 1/1992 | Efron et al. | 359/41 |
| 5,085,498 | 2/1992 | Yamamoto et al. | 359/70 |
| 5,298,732 | 3/1994 | Chen | 250/203.4 |
| 5,353,080 | 10/1994 | Christman | 354/154 |
| 5,420,709 | 5/1995 | Kato et al. | 359/72 |
| 5,608,567 | 3/1997 | Grupp | 359/275 |

FOREIGN PATENT DOCUMENTS

| | | |
|---|---|---|
| 2 626 385 | 7/1989 | France . |
| 2 655 163 | 5/1991 | France . |
| 2 661 755 | 11/1991 | France . |
| 2 014 179 | 11/1974 | Germany . |
| 33 28 436 | 4/1984 | Germany . |
| 34 37 704 | 7/1985 | Germany . |
| 37 21 751 | 1/1989 | Germany . |
| 689 03 393 | 3/1993 | Germany . |
| 43 05 807 | 10/1994 | Germany . |

OTHER PUBLICATIONS

Patent Abstracts of Japan 4–141626 (A), P–1413, Sep. 3, 1992, vol. 16, No. 418.

Patent Abstracts of Japan 1–302226 (A), P–1010, Feb. 21, 1990, vol. 14, No. 94.

Patent Abstracts of Japan 60–230121 (A), P–446, Apr. 15, 1986, vol. 10, No. 97.

Patent Abstracts of Japan 60–254120 (A), P–456, May 16, 1986, vol. 10, No. 132.

Patent Abstracts of Japan 07306421(A) Nov. 21, 1995.

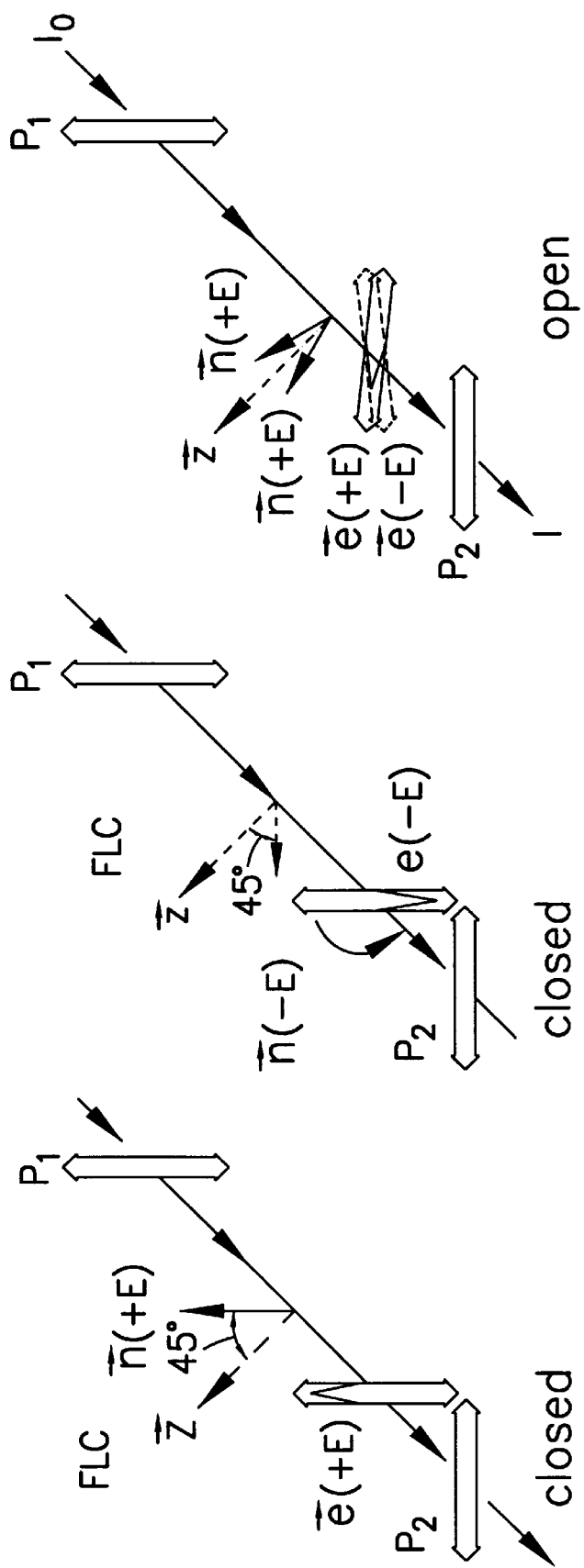

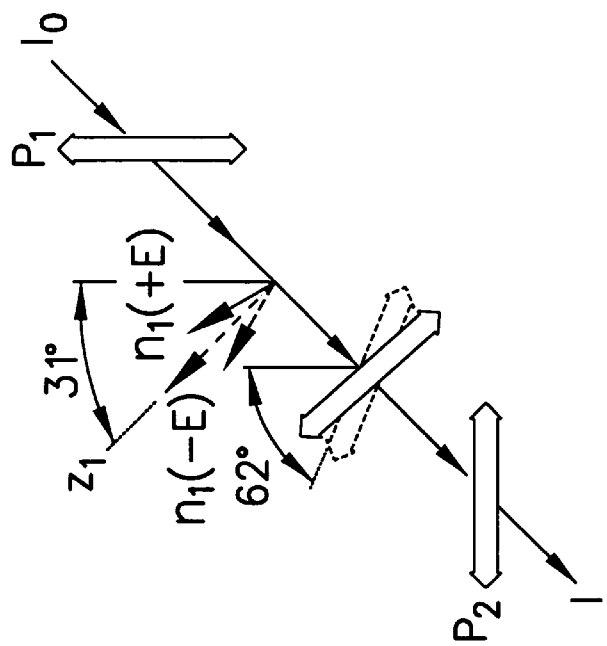
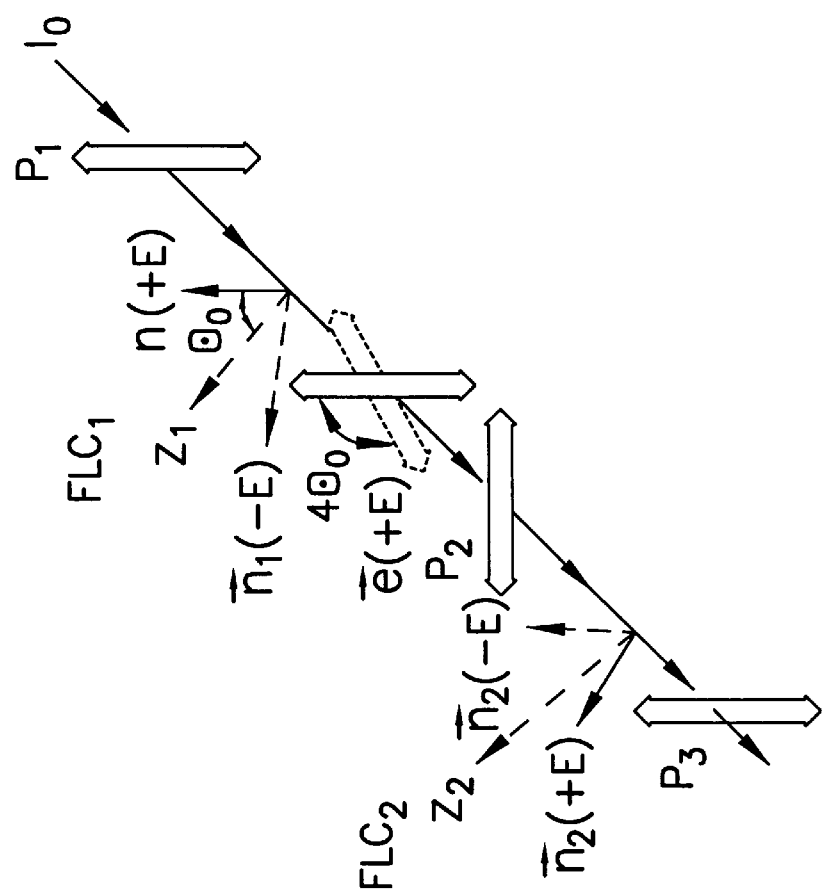
Fig. 3b
Fig. 3a

FERROELECTRIC LIQUID CRYSTAL DEVICE FOR LOCAL REDUCTION OF LIGHT INTENSITY IN THE VISUAL FIELD

FIELD OF THE INVENTION

The present invention relates to a device for locally reducing the light intensity in the visual field of the human eye, of video or still cameras or the like.

BACKGROUND INFORMATION

In present-day communications, optical methods for transmitting and processing information are attractive and promising, since they offer extraordinary advantages over all other types of communication methods. It is necessary to view and register optical images using the eye, video cameras and other light-sensitive devices in order to record optical information provided by light sources of different intensities (e.g., lasers, the sun, lamps, etc.)

Photosensitive media must be protected against being blinded and possibly damaged by incident light of excessive intensity. Safety devices normally used for this purpose have numerous disadvantages: neutral or polarizing filters also diminish the brightness of the objects to be observed, together with that of the interfering light. If the lighting is diminished, these filters are mechanically removed. Known eyeglasses, switched automatically to absorbing filters by strong incident light, reduce the overall visual field. A better protection is offered by locally reducing the brightness of strongly illuminated objects situated in the visual field of the eye, video camera, etc., without suppressing poorly illuminated objects at the same time.

One solution is provided by Optically Addressed Spatial Light Modulators (OASLM). Safety glasses using optically addressed spatial light modulators (OASLM) are described by M.G. Tomilin, A.P. Onokhov, and D. Yu. Polushkin in Mol. Cryst., Liq. Crys., 222, 119, (1992). In this case, the twisting effect in nematic liquid crystals is used as the medium affecting the light. The basic disadvantage of the use of nematic liquid crystals is their relatively slow switching time (approx. $10^{-2}$s). This results in blurring of the suppressed image during the motion of bright objects in optically addressed spatial light modulators (OASLM) or the blinding of the eye or the video camera.

SUMMARY OF THE INVENTION

An object of the present invention is to provide an improved and faster device for locally reducing light intensity for different applications, using the deformation of the ferroelectric helix.

The present invention therefore provides a device for local reduction of light intensity in the visual field of the human eye, video or still cameras or the like, or light-sensitive devices for observing and recording illuminated images, comprising lenses and filters, characterized in that an optically addressed spatial light modulator (OASLM) is arranged between a compound lens consisting of one or more lenses ($L_1$) and two polarizers ($P_1$ and $P_2$), which optically addressed spatial light modulator (OASLM) comprises two transparent plates with electrodes, a semitransparent photoconducting layer (PC) and a helix-shaped smectic liquid crystal (FLC), arranged between the plate in bookshelf and/or deformation domain geometry with the helix axis of the smectic liquid crystal parallel to the plates.

Further features include that the smectic liquid crystal (FLC) is located in the inclined smectic C phase and that the optical properties of the smectic liquid crystal (FLC), illuminated by high-intensity light, can be controlled so that the light is not transmitted through the device for at least one polarity of the voltage applied to the electrodes.

Moreover, a shutter may be provided to prevent the light from being transmitted through the device for the reverse polarity of the voltage applied to said electrodes. The shutter (2) may be designed as an additional ferroelectric liquid crystal layer ($FLC_2$) located between two transparent plates provided with electrodes and positioned between one of said polarizing layers or polarizers ($P_1$, $P_2$) and a third polarizing layer or polarizer ($P_3$).

The other ferroelectric liquid crystal may be located in a chiral smectic C or smectic A phase. The second chiral smectic liquid crystal layer located between two additional transparent plates provided with electrodes may be arranged between the optically addressed spatial light modulator (OASLM) and the polarizing layer (PC). The optical characteristics of the additional chiral smectic liquid crystal, when brightly illuminated, are adjusted for both voltage polarities applied to the electrodes, so that light transmission through the device is blocked. The smectic liquid crystal in the ferroelectric smectic C phase may have a molecular inclination of $45°-\theta_o$ or $\theta_o$, which is the molecular inclination of said smectic liquid crystal in the optically addressed spatial light modulator (OASLM).

In the device proposed in the present invention, use is made of a much faster electrooptical effect in ferroelectric liquid crystals, namely the deformation of the ferroelectric helix (DHF effect), described by L. A. Beresnev, V. G. Chigrinov, D. I. Dergachev, E. P. Pozhidaev, J. Finfschiling, and M. Schadt in Liquid Crystals, 5, p. 1171 (1989) which is hereby incorporated in its entirety by reference. This effect is characteristic for chiral smectic C materials with a very small helix pitch $p_0$ (0.3 μm or less), and offers considerable advantages compared to the electrooptical effects in nemates.

The safety device according to the present invention is considerably faster than devices based on nematic liquid crystals. The operating frequency is in the range of approximately $10^2$ to $10^3$ Hz, rather than 1–20 Hz for nemates. Thus blurring of the image during observation of moving illuminated objects and blinding of the eye or the video camera is avoided.

BRIEF DESCRIPTION OF THE DRAWINGS

FIGS. 2a–c show the use of a DHF-LC material with a molecular inclination $\theta_o=45°$ according to an embodiment of the present invention.

FIGS. 3a–b show the use of a DHF-LC material with a molecular inclination $\theta_o<45°$ according to an embodiment of the present invention.

The following reference symbols and respective concepts are used in the description below and the drawings:

| | |
|---|---|
| 1 | eye and/or video camera |
| 2 | shutter |
| 3 | compensator |
| $L_{1-3}$ | lenses |
| $P_{1-3}$ | polarizers |
| PC | photoconductor |
| FLC | ferroelectric liquid crystals |
| OASLM | optically addressed spatial light modulators |
| E | voltage |

DETAILED DESCRIPTION

Figure 1:
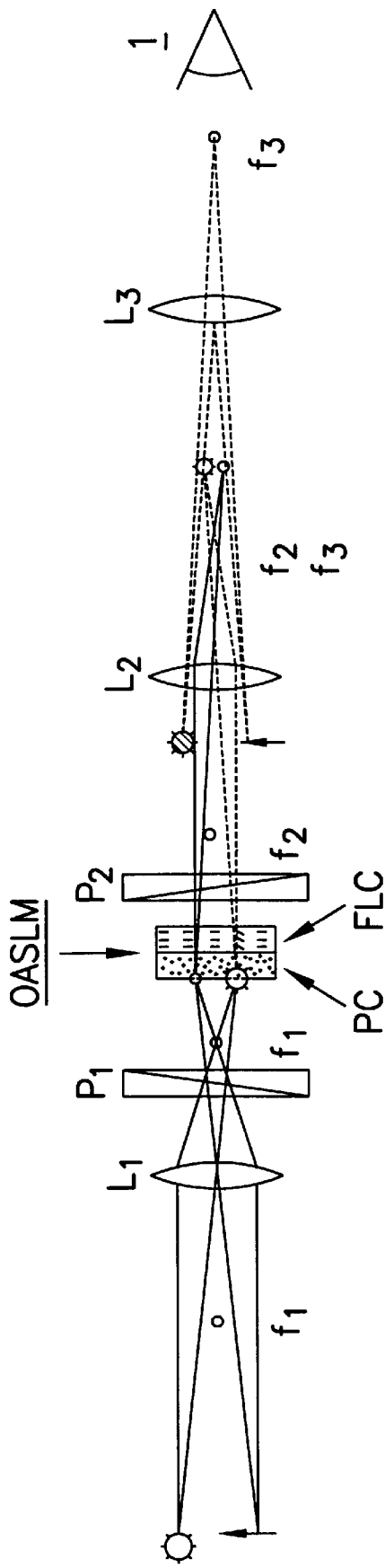
FIG. 1 shows a general view of an eyeglass lens with local reduction of high light intensities according to an embodiment of the present invention.

FIG. 1 shows a general view of an eyeglass lens with local reduction of high light intensities using optically addressed spatial light modulators (OASLM) according to an embodiment of the present invention. It comprises in addition to lenses $L_1$, $L_2$, $L_3$, polarizers $P_1$, $P_2$, photoconductors PC and ferroelectric liquid crystals FLC. The following scenario is assumed as a starting point: a brightly illuminated image—such as the sun; and a poorly illuminated image—such as a house. After passing through polarizer $P_2$, the intensity of the sun's image is reduced compared to that of the house.

A detailed description of the principle and the operation of the device, as well as of its individual components, follows using FIG. 1.

The optically addressed spatial light modulator (OASLM) illustrated in FIG. 1 is based on a photoconductive layer PC and a liquid crystal film FLC. When the nematic layer TN adjacent to the photoconductive layer PC is twisted, the light from poorly illuminated objects ("house") can pass through crossed polarizers $P_1$ and $P_2$. The light from brightly illuminated objects ("sun") is focused on the PC layer, inducing the local transition from twisted to homeotropic state in the FLC layer due to the voltage externally applied to the optically addressed spatial light modulator (OASLM). The twisted-homeotropic transition is completed only at the location of the optically addressed spatial light modulator (OASLM) where the conductivity of photoconductor PC increases due to the strong lighting ("sun"). At this point the light does not pass through polarizer $P_2$; the brightness of the strongly illuminated object ("sun") is reduced in the resulting image. Lenses $L_2$ and $L_3$ represent the simplest "eye" 1 for observing this image. The optical design of the system can be more complex depending on the required size and shape of the eyeglasses (prisms, mirrors, etc. can be used).

Referring to FIGS. 2a–c, three extreme states of the average optical indicatrix <n> occur in the optically addressed spatial light modulator (OASLM) when the DHF effect is used, as described by B. I. Ostrovski, A. Z. Rabinovich, and V. G. Chigrinov in "Advances in Liquid Crystal Research and Applications," published by L. Bata, Pergamon Press, Oxford—Akad. Kiadó, Budapest—1980, p. 469, and which is herein incorporated by reference: (1) for positive voltage +E (open), the deviation of n is equal to $+\theta_o$ in relation to direction z; (2) for negative voltage –E (open) the optical axis n is deflected by $-\theta_o$, where $\theta_o$ is the molecular inclination in smectic phase C* and n is the direction of the longitudinal molecular axis (director); and (3) for low voltages the axis <n> of the average optical design indicatrix is deflected by a small amount, in proportion to the voltage applied from the z direction.

Two extreme positions $+\theta_o$ and $-\theta_o$ occur for the brightly illuminated areas of the optically addressed spatial light modulator (OASLM). Thus the externally applied voltage, acting upon the FLC layer, exceeds the threshold value for winding up the helix.

FIG. 2 shows the effect when DHF LC material with a molecular inclination of $\theta_o=45°$ is used. FIGS. 2a, and 2b show the plane of polarized light $e(\pm E)$ for positive (FIG. 2a) and negative (FIG. 2b) polarity of the drive voltage, respectively. For brightly illuminated areas of the optically addressed spatial light modulator (OASLM), light is not allowed to pass. FIG. 2c is a small deviation of the planes of $e(\pm E)$ from the original direction z of the helix axes (equaling the direction of friction) for light emitted from the poorly illuminated areas of the optically addressed spatial light modulator (OASLM).

In one arrangement of the FLC layer with a molecular inclination of $\theta_o = 45°$ according to FIGS. 2a and 2b, high light intensity is suppressed for both polarities of the drive voltage if the direction of friction z forms an angle of 45° with polarizer $P_1$. In the poorly illuminated areas of the optically addressed spatial light modulator (OASLM), the average optical indicatrix is almost parallel to the direction of the undisturbed helix z (FIG. 2c), which results in almost all the light being transmitted. The polarization plane of the light $e(\pm E)$ is rotated by 90°.

FIG. 3 shows the operation when using DHF LC material with a molecular inclination of $\theta_o<45°$. FIGS. 3a and 3b denote the planes of the polarized light $e(\pm E)$ for positive and negative polarity of the drive voltage in brightly (FIG. 3a) and poorly (FIG. 3b) illuminated areas of the optically addressed spatial light modulator (OASLM). For positive polarity $e(+E)$, the director $n_1$ runs in the $FLC_1$ layer. For negative polarity $e(-E)$, the director $n_2(-E)$ of shutter 2 (shown in FIG. 4) coincides with polarizer $P_2$. Thus no light passes through polarizer $P_3$.

Figure 4:
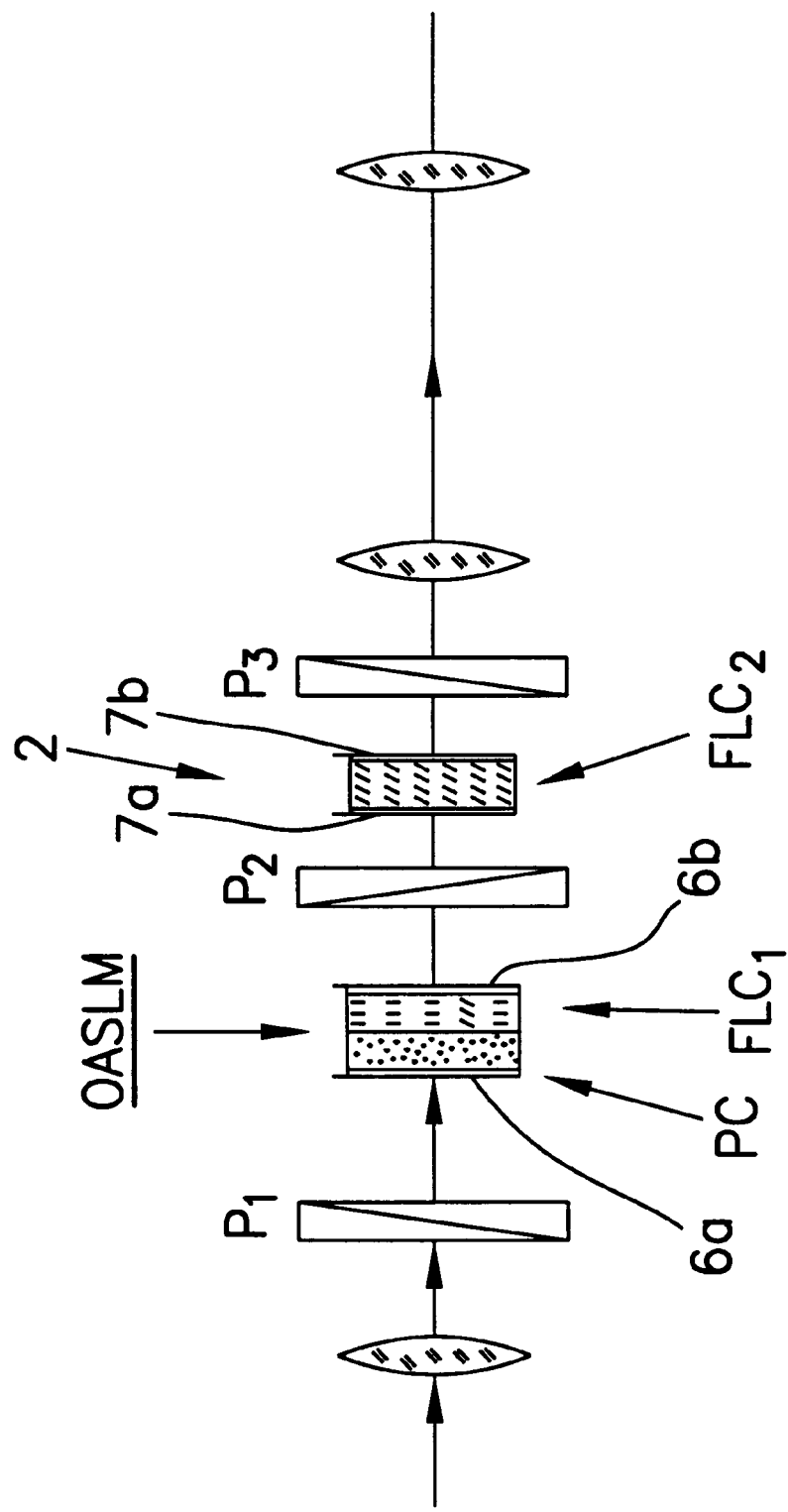
FIG. 4 shows the optical diagram of a fast-shutter eyeglass lens according to an embodiment of the present invention.

FIGS. 3 and 4 illustrate the case of $\theta_o \neq 45°$. For positive polarity +E of the drive voltage, the transmitted light in the brightly illuminated areas is fully suppressed by the optically addressed spatial light modulator (OASLM), FIG. 3a. For negative polarity of the drive voltage, quick shutter 2 (FIG. 4) is used to avoid blinding of the eye and/or the video camera 1. FIG. 4 also shows the optically addressed spatial light modulator (OASLM) with its transparent plates 6a, 6b with electrodes, and the quick shutter 2 with transparent plates 7a, 7b with electrodes.

Figure 5:
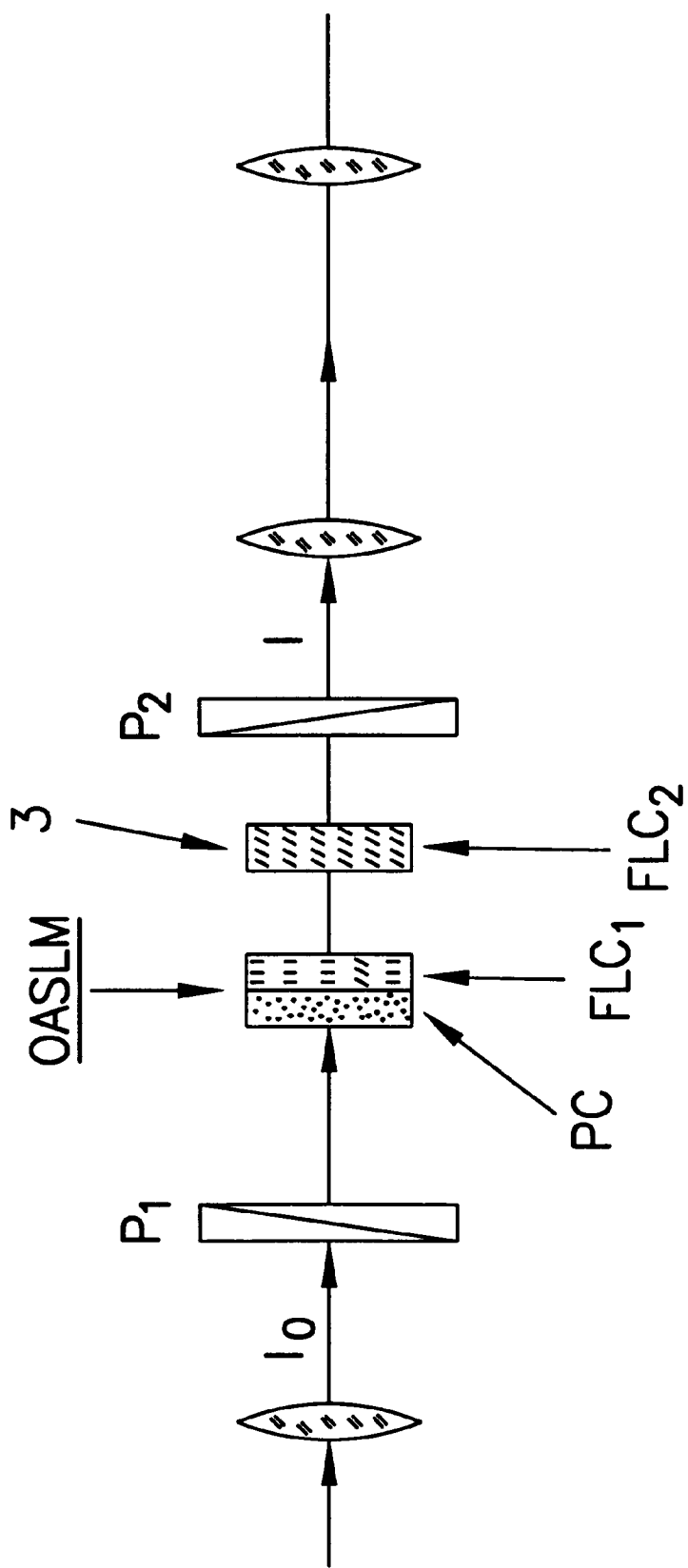
FIG. 5 shows the optical diagram of an eyeglass lens with fast-switching "compensator" $FLC_2$ according to an embodiment of the present invention.

FIG. 5 shows the optical diagram of the eyeglass lens or device with quick-switching "compensator" 3, where layer $FLC_1$ has a molecular inclination of $\theta_o=45°$. The second layer $FLC_2$ operates as a switchable "compensator" 3, which rotates the polarization plane $e(-E)$ of the light coming from the brightly illuminated surfaces of the photoconductor in the $FLC_1$ layer back in the direction $U_1(+E)$. In this case, the brightly illuminated images are fully suppressed for both polarities of the meander voltage.

FIGS. 6a–c and 7a–c show the diagram of the optical deformations in the device with the ferroelectric smectic liquid crystal of a C phase with a molecular inclination of $\theta_c=45°-\theta_o$ and $\theta_c=\theta_o$, respectively, used as a compensator.

Figures 6A, 6B, 6C:
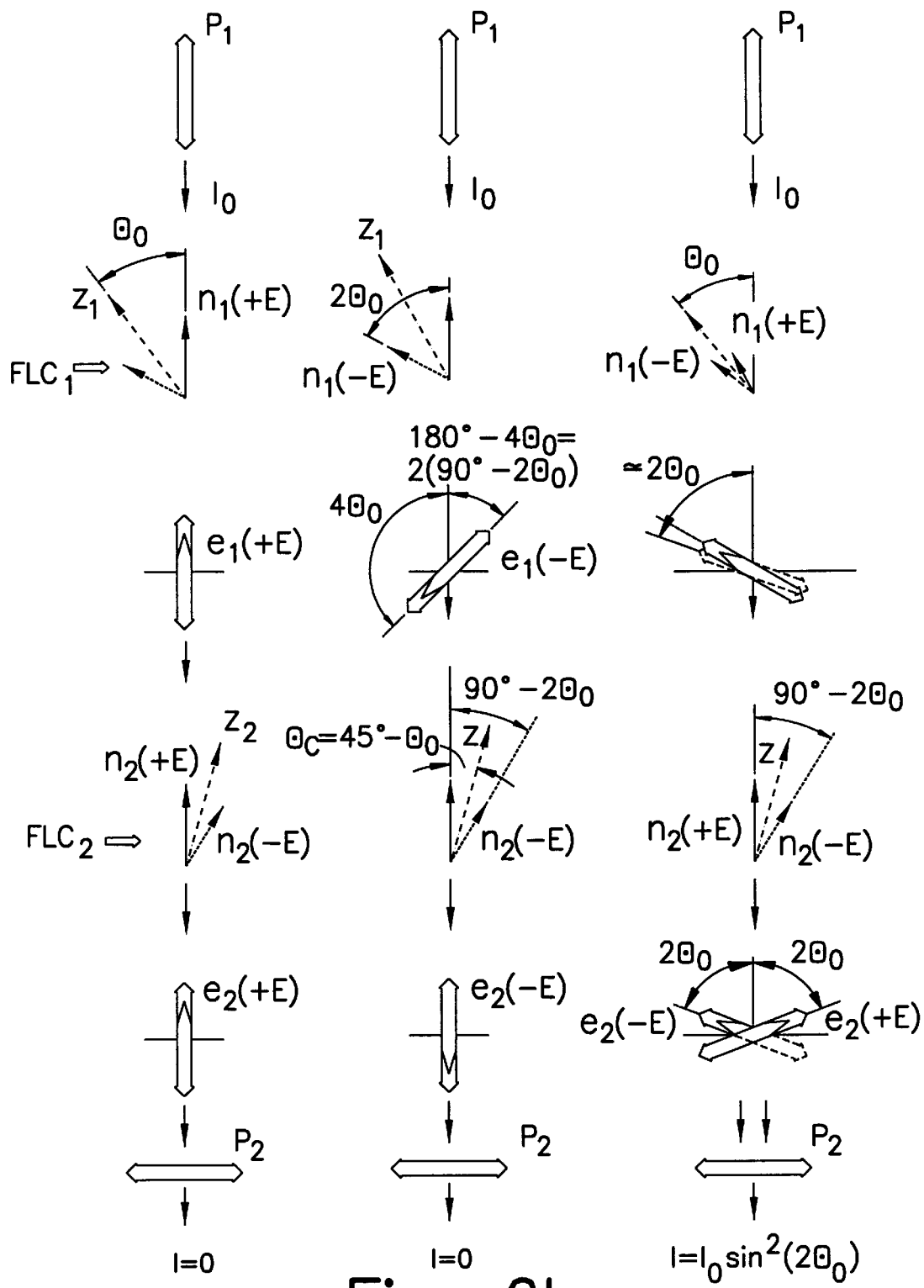
FIGS. 6a–c show the use of an $FLC_2$ compensator with a molecular inclination $\theta_c=45°-\theta_o$ according to an embodiment of the present invention.
Figures 7A, 7B, 7C:
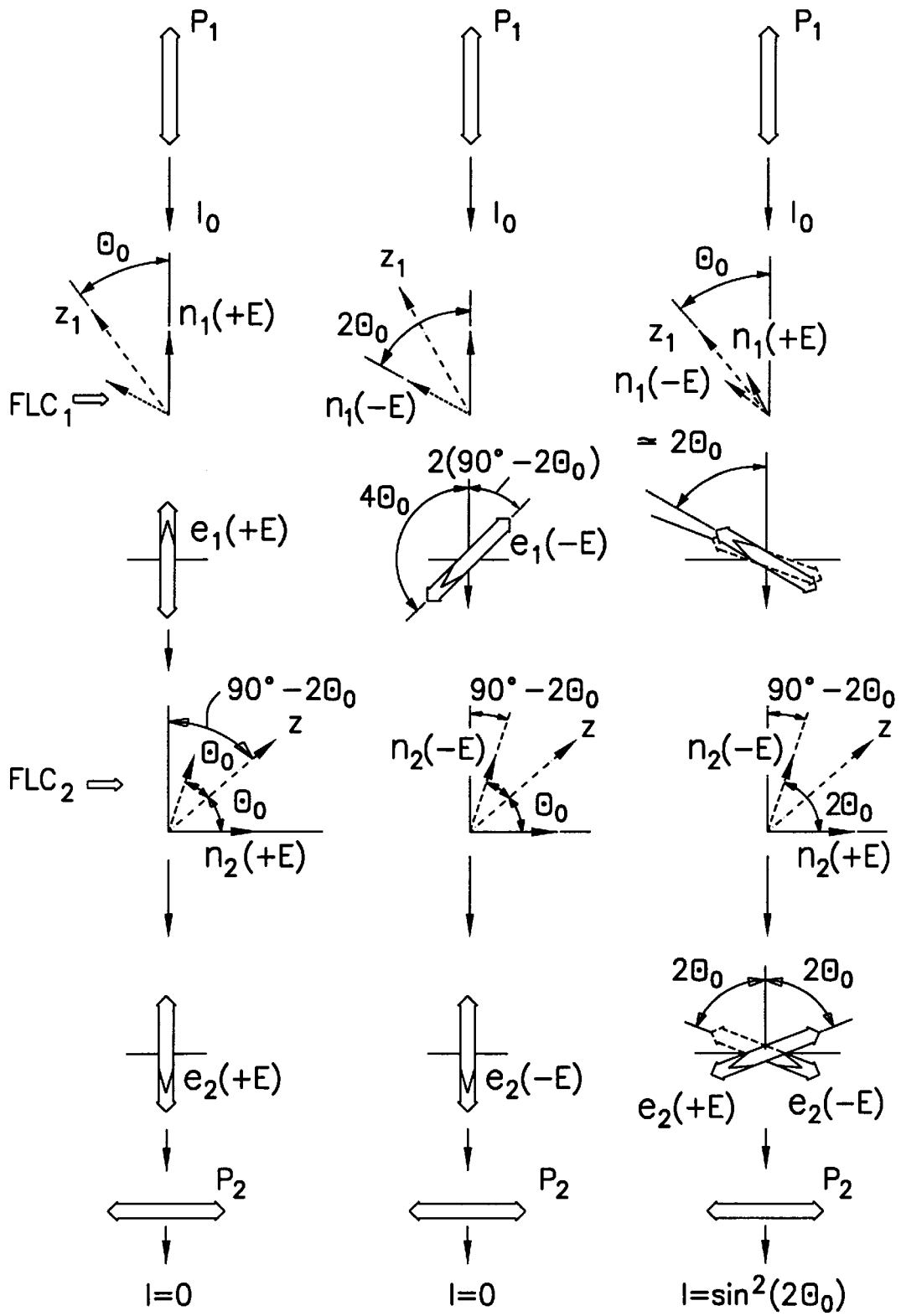
FIGS. 7a–c shows the use of an $FLC_2$ compensator with a molecular inclination $\theta_c=\theta_o$ according to an embodiment of the present invention.

FIGS. 6a and b show the position of director $n_1(\pm E)$ of the first layer $FLC_1$. Illustrated is the plane of the polarized light $e_1(\pm E)$, which passes through layer $FLC_1$ due to the positive or negative polarity of the applied voltage E in brightly illuminated zones of the optically addressable, spatial light modulator (OASLM), and $n_2(\pm E)$ is the corresponding position of director $n_2$ of the $FLC_2$ layer (corresponding to compensator 3). In the case of both polarities, the plane of the polarized light $e_2(\pm E)$, passing through the $FLC_2$ layer, is perpendicular to that of polarizer $P_2$. Therefore, passage of light is blocked in the brightly illuminated areas of the optically addressable, spatial light modulator (OASLM).

FIG. 6c shows the small deviation of director $n_1(\pm E)$ from the direction $z_1$ of the helix axis in the $FLC_2$ layer in poorly illuminated areas of the optically addressed spatial light modulator (OASLM). Intensity I of the light coming from these areas is equal to $I \sim I_o \sin^2(2\theta_0)$ for both voltage polarities. $I_o$ is the intensity of the light impinging on the optically addressed spatial light modulator (OASLM).

FIG. 7 shows an application of the $FLC_2$ compensator 3 with a molecular inclination of $\theta_c$—$\theta_o$. The resulting intensity I of the light exiting from the poorly illuminated areas of the optically addressed spatial light modulator (OASLM) through polarizer $P_2$ is $I = I_o \sin_2(2\theta_o)$. Compared with the case where $\theta_c = 45° - \theta_o$, the light wave only undergoes a 180° phase shift.

In the cases illustrated in FIGS. 6a–c and 7a–c, the thickness of both FLC layers meets the condition $\Delta nd = \lambda/2 + N\lambda$, where $\lambda$ is the light wavelength. The electroclinic material, for example the chiral smectic A-phase having a relatively small induced inclination $\theta_c = 5° + 10°$ can be used as a "compensator" $FLC_2$. The required value of the angle $\theta_c = 45° - \theta_o$ can be adjusted by changing the voltage amplitude used on the $FLC_2$ layer.

The operation of the safety device based on the optical diagram with "shutter" 2, shown in FIGS. 3 and 4 is shown as an illustrative example of a device for locally reducing light intensity according to according to an embodiment of the present invention. Optically addressed spatial light modulators (OASLM), used in this diagram, comprise two quartz plates with transparent indium-zinc oxide electrodes. In one of the electrodes, a quasi-amorphous 1 $\mu$m thick ZnSe film is used as the photoconductive layer and denoted as PC in FIG. 4. A polyvinyl alcohol film was applied on a round substrate with a diameter of 35 mm using a spin coating process to achieve optical homogeneity of the FLC layer. After treatment of the polymer film at 130° C., it was rubbed with a cotton cloth in one direction. The distance between the $FLC_1$ and $FLC_2$ cells was approximately 5.5 $\mu$m, resulting in the optical condition $\Delta n^* d = 3\lambda/2$ for the green range of the light.

The $FLC_1$ and $FLC_2$ cells were filled with the isotropic phase of the FLC material and cooled to room temperature. The basic parameters of the DHF material used are:
Phase transitions Cr.(<–10° C.)$S^*_c$(59° C.)Is;
Spontaneous polarization $P_s \sim 200$ nC*cm$^{-2}$;
helix pitch $p_o \sim 0.27$ $\mu$m; and
inclination $\theta_o = 31°(20°$ C.).

Considerable optical homogeneity was achieved for both FLC layers (the average contrast was 200 on a surface area of >5 cm$^2$) when alternating voltage with an amplitude of ±50 V and a frequency of 10–1000 Hz was used at the same time and the substrates were precisely trimmed in relation to one another in a direction perpendicular to the direction of rubbing. In this case the FLC layer has exact "bookshelf" geometry for relatively small values of spontaneous polarization or the geometry of a "dislocation domain structure" for higher spontaneous polarization as described by L. A. Beresnev, E. Schumacher, S. A. Pikin, Z. Fan, B. I. Ostrovsky, S. Hiller, A. P. Onokhov and W. Haase in Jpn. J. Appi. Phys., Vol. 34, Part 1, No. 5A, May 1995 and which is herein incorporated by reference.

FIG. 8a shows a selected image of test target image 0683, focused on the optically addressed spatial light modulator (OASLM), based on ZnSe+DHF; thickness of the FLC layer is 5.5 $\mu$m, amplitude of the AC (meander) voltage applied is ±7.5 V, its frequency is 50 Hz. The image size is 1.5×1.5 mm. The numbers 100, 200, 150 in the pictures correspond to spatial resolutions of 20, 40, and 30 pl/mm, respectively. FIGS. 8b–d show a selected image of the test target image, which can be registered with a moving optically addressed spatial light modulator (OASLM). The optically addressed spatial light modulator (OASLM) moves downward. FIG. 8b–1.5 mm/s; FIG. 8c–4.5 mm/s; and FIG. 8d–6.5 mm/s. The interval between the images is 40 ms. The point in the square belongs to the optically addressed spatial light modulator (OASLM) and serves as a reference point.

Figure 8:
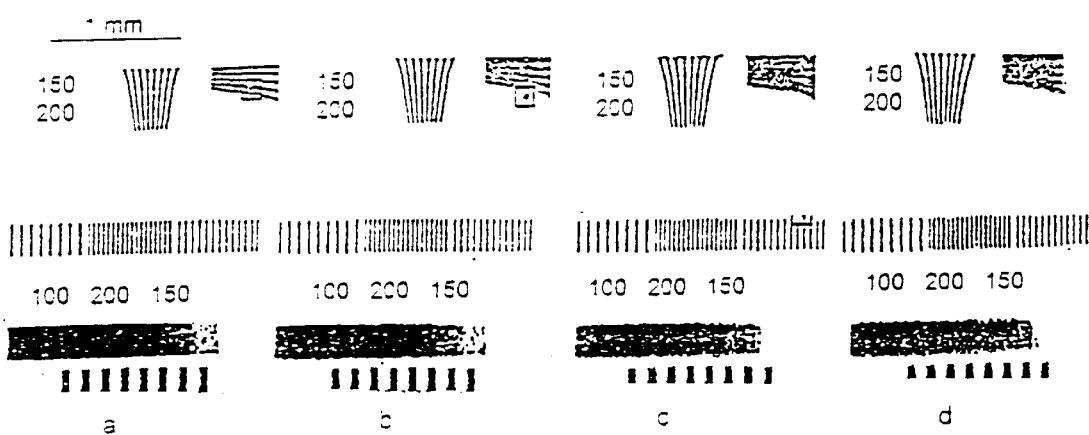
FIGS. 8a–d show the selected image of the test target image 0683 according to an embodiment of the present invention.

FIG. 8 describes the basic features of the optically addressed spatial light modulator (OASLM) manufactured. Blue light was used for recording the test target image and red light for reading the resulting image. A square wave drive voltage (meander) with an amplitude of ±7.5 V and a frequency of 50 Hz was used. The spatial resolution of the optically addressed spatial light modulator (OASLM) thus obtained is greater than 40 pl/mm for a modulation depth of approx. 50%. The resolution for one polarity only of the drive voltage can be higher than 100 pl/mm for the same modulation depth. The limit value is given by the optical setup of the projection.

FIGS. 8b–d show the readout images with moving optically addressed spatial light modulator (OASLM) in relation to the test target image. It can be seen that up to a motion speed of 8 mm/s the image is relatively unblurred, which can also be explained by the method of recording the video image.

To test the operation of the eyeglass lens, a 100 W tungsten-halogen lamp was used as a very bright image. A white sheet of paper with the word "goggles" written on it was placed behind the lamp. A green filter was placed between lens $L_3$ and the video camera to suppress the infrared and ultraviolet portions of the light spectrum, which pass through polarizers $P_1$ and $P_3$. The optical shutter parameters were: $f_1 = 5$ cm, $f_2 = 2$ cm, and $f_3 = 1$ cm (see FIG. 1).

Figure 9:
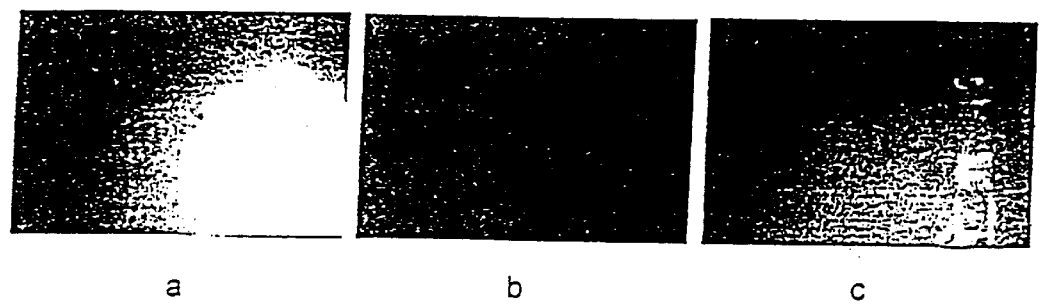
FIGS. 9a–c shows the operation of a safety device according to an embodiment of the present invention with local brightness reduction of images of strongly illuminated objects.

FIG. 9 shows the mode of operation of the safety device with local brightness reduction of the images of brightly illuminated objects, using optically addressed spatial light modulators (OASLM) on the basis of a 1 $\mu$m thick photoconducting film (ZnSe), using the DHF effect in FLCs, where the FLC layer was 5.5 $\mu$m thick. A diagram "with shutter" (see also FIGS. 3 and 4) is shown in FIG. 9a—where no voltage is applied to the optically addressed spatial light modulator (OASLM), the shutter is open, and the video camera is strongly blinded; FIG. 9b—where the shutter is closed and the light path is barely observable; and FIG. 9c—where the shutter is open, a voltage applied to the optically addressed spatial light modulator (OASLM) is +10 V, and the brightness of the lamp filament is considerably suppressed, yet the object behind the lamp (sheet with the word "goggles") is visible without blinding (the meander voltage is ±10 V, 1 Hz).

FIG. 9 shows that the brightness of an intensely illuminated object (lamp filament) is effectively suppressed when an electric voltage is applied to the optically addressed spatial light modulator (OASLM), while the brightness of the less intensely illuminated objects (sheet with the word "goggles") is not suppressed. Thus the text is clearly visible without the video camera being blinded. This is contrasted with the same image when no voltage is applied to the optically addressed spatial light modulator (OASLM). In that case, the lamp is too bright for the text to be read, since the video camera is blinded.

For the device to function properly, the shutter $FLC_2$ of the device closes 5–10 ms after the reaction of the optically addressed spatial light modulator (OASLM). At the same time, the polarity of the voltage applied to the optically addressed spatial light modulator (OASLM) is reversed. The entire cycle is repeated after 10–20 ms. The device operates at a meander frequency of up to 1 kHz if the bias field has been fine tuned and the optically addressed spatial light modulator (OASLM) is between the cross polarizers $P_1$ and $P_2$. These high frequencies allow the movement of poorly illuminated objects to be observed against the background of brightly illuminated objects such as the sun, lamp, etc., without blurring the images or blinding the eye or video camera 1. The device can be successfully used not only in optical control devices in optical telecommunication links, but also in welding and cutting operations, as well as other activities where high local light intensities occur.

What is claimed is:

1. A device for the local reduction of light intensity in visual fields, the device comprising:
   a compound lens having at least one lens and two polarizers;
   an optically addressed spatial light modulator (OASLM) arranged between the two polarizers of the compound lens, the optically addressed spatial light modulator (OASLM) having two transparent plates each with at least one electrode, a semitransparent photoconducting layer (PC), and a helix-shaped ferroelectric liquid crystal (FLC),
   wherein the helix-shaped ferroelectric liquid crystal (FLC) is arranged between the two transparent plates in one of a bookshelf geometry and a deformation domain geometry, such that a helix axis of the helix-shaped ferroelectric liquid crystal (FLC) is parallel to an orientation of the two transparent plates.

2. The device as recited in claim 1 wherein the helix-shaped ferroelectric liquid crystal (FLC) is located in an inclined smectic C phase.

3. The device as recited in claim 1 wherein a plurality of optical properties of the helix-shaped ferroelectric liquid crystal (FLC), when illuminated by a high-intensity light, can be controlled so that the high-intensity light is not transmitted through the device for at least one polarity of a voltage applied to the at least one electrode.

4. The device as recited in claim 1 further comprising:
   a shutter for preventing the high-intensity light from being transmitted through the device when a reverse polarity of a voltage is applied to the at least one electrode.

5. The device as recited in claim 4 wherein the shutter is designed as a second ferroelectric liquid crystal ($FLC_2$) located between two further transparent plates and being positioned between one of the two polarizers and a third polarizer.

6. The device as recited in claim 4 wherein the second ferroelectric liquid crystal ($FLC_2$) is located in one of a chiral smectic C phase and a chiral smectic A phase.

7. The device as recited in claim 1 further comprising a second ferroelectric liquid crystal ($FLC_2$) located between two further transparent plates each provided with at least one electrode, wherein the second ferroelectric liquid crystal ($FLC_2$) is arranged between the optically addressed spatial light modulator (OASLM) and one of the two polarizers.

8. The device as recited in claim 7 wherein a plurality of optical characteristics of the second ferroelectric liquid crystal ($FLC_2$), when the second ferroelectric liquid crystal ($FLC_2$) is brightly illuminated, are adjusted for both a positive and a negative voltage polarity applied to the at least one electrode of the second pair of transparent plates, so that a light transmission through the device is blocked.

9. The device as recited in claim 7 wherein the second ferroelectric liquid crystal ($FLC_2$), when located in a smectic C phase, has a molecular inclination of 45° of one of either $-\theta_o$ and $\theta_o$, and is the same as a molecular inclination of the helix-shaped ferroelectric liquid crystal (FLC) in the optically addressed spatial light modulator (OASLM).

10. The device as recited in claim 7 wherein the second ferroelectric liquid crystal ($FLC_2$) is located in a chiral smectic A phase.

* * * * *